(12) United States Patent
Chen et al.

(10) Patent No.: US 8,183,189 B2
(45) Date of Patent: May 22, 2012

(54) PREPARATION OF A SULFURIZED MOLYBDENUM AMIDE COMPLEX AND ADDITIVE COMPOSITIONS HAVING LOW RESIDUAL ACTIVE SULFUR

(75) Inventors: Qunlai Chen, Walnut Creek, CA (US); Man Hon Tsang, Oakland, CA (US); Gaurav Bhalla, Hercules, CA (US); William R. Ruhe, Jr., Benicia, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 191 days.

(21) Appl. No.: 12/570,974

(22) Filed: Sep. 30, 2009

(65) Prior Publication Data

US 2011/0077180 A1 Mar. 31, 2011

(51) Int. Cl.
*C10M 159/18* (2006.01)
*C01G 39/06* (2006.01)

(52) U.S. Cl. ........................................ 508/362; 508/167
(58) Field of Classification Search ................. 508/362, 508/167
See application file for complete search history.

(56) References Cited

U.S. PATENT DOCUMENTS

| | | |
|---|---|---|
| 3,405,064 A | 10/1968 | Miller |
| 3,419,589 A | 12/1968 | Larson et al. |
| 3,494,866 A | 2/1970 | Rowan et al. |
| 3,509,051 A | 4/1970 | Farmer et al. |
| 4,098,705 A | 7/1978 | Sakurai et al. |
| 4,259,194 A | 3/1981 | deVries et al. |
| 4,259,195 A | 3/1981 | King et al. |
| 4,261,843 A | 4/1981 | King et al. |
| 4,263,152 A | 4/1981 | King et al. |
| 4,289,635 A | 9/1981 | Schroeck |
| 4,705,643 A | 11/1987 | Nemo |
| 5,468,891 A | 11/1995 | Udding et al. |
| 6,174,842 B1 | 1/2001 | Gatto et al. |
| 6,358,894 B1 | 3/2002 | Leta et al. |
| 6,509,303 B1 | 1/2003 | Gatto |
| 6,914,037 B2 | 7/2005 | Gatto |
| 6,962,896 B2 | 11/2005 | Ruhe, Jr. et al. |
| 2002/0038525 A1 | 4/2002 | Callis et al. |
| 2003/0166477 A1* | 9/2003 | Abraham et al. ............. 508/198 |
| 2004/0132627 A1 | 7/2004 | John et al. |
| 2005/0209111 A1* | 9/2005 | Ruhe et al. .................... 508/242 |

OTHER PUBLICATIONS

PCT International Search Report—PCT/US2009/059083—Date of mailing Jun. 18, 2010.

* cited by examiner

*Primary Examiner* — Walter D Griffin
*Assistant Examiner* — Francis C Campanell
(74) *Attorney, Agent, or Firm* — Joseph P. Foley

(57) ABSTRACT

The invention is directed to oil soluble additive compositions, lubricating oil compositions derived from a process for preparing a sulfurized oil soluble molybdenum complex having reduced active sulfur comprising: reacting an acidic molybdenum compound with an amide derived from a carboxylic acid component an polyamine component in a ratio from 2:1 to 1:1; there after sulfurizing to provide a sulfurized oil soluble molybdenum which is subsequently treated with at least one compound capable of reacting with the active sulfur of step b).

22 Claims, No Drawings

PREPARATION OF A SULFURIZED MOLYBDENUM AMIDE COMPLEX AND ADDITIVE COMPOSITIONS HAVING LOW RESIDUAL ACTIVE SULFUR

FIELD OF THE INVENTION

This invention relates to new lubricating oil additives and lubricating oil compositions. More specifically, it relates to new lubricating oil compositions containing a friction reducing component comprising a sulfurized molybdenum amide complex having low residual active sulfur.

BACKGROUND OF THE INVENTION

Molybdenum disulfide has long been known as a desirable additive for use in lubricating oil compositions. Molybdenum disulfide is ordinarily finely ground and then dispersed in the lubricating oil composition to impart friction modifying and antiwear properties. However, one of the major detriments to using finely ground molybdenum disulfide is its lack of solubility.

As an alternative to using finely ground molybdenum disulfide as a friction modifier, a number of other approaches involving various salts of molybdenum compounds have been employed. Molybdenum dithiocarbamates (MoDTC) and molybdenum dithiophosphates (MoDTP) are well known in the art to impart friction modifying properties. Representative compositions of MoDTC are described in Larson et al., U.S. Pat. No. 3,419,589, which teaches molybdenum (VI) dioxide dialkyldithiocarbamates; Farmer et al., U.S. Pat. No. 3,509,051, which teaches sulfurized oxymolybdenum dithiocarbamates; and Sakurai et al., U.S. Pat. No. 4,098,705, which teaches sulfur containing molybdenum dihydrocarbyl dithiocarbamate compositions. Representative compounds of MoDTP are the compositions described in Rowan et al., U.S. Pat. No. 3,494,866, such as oxymolybdenum diisopropylphosphorodithioate.

Another method of incorporating molybdenum compounds in oil is to prepare a colloidal complex of molybdenum disulfide or oxysulfides dispersed using known dispersants. Known dispersants include basic nitrogen containing compounds including succinimides, carboxylic acid amides, phosphonoamides, thiophosphonoamides, Mannich bases, and hydrocarbonpolyamines. King et al., U.S. Pat. No. 4,263,152; King et al., U.S. Pat. No. 4,261,843; and King et al., U.S. Pat. No. 4,259,195 teach molybdenum compounds used as anti-oxidant and anti-wear additives comprising an acidic molybdenum compound and a basic nitrogen compound which acts as a dispersant.

DeVries et al., U.S. Pat. No. 4,259,194 discloses a sulfur containing additive comprising the reaction product of ammonium tetrathiomolybdate and a basic nitrogen compound for use as an anti-oxidant, anti-wear agent, and friction modifier.

Nemo, U.S. Pat. No. 4,705,643 teaches the preparation of carboxylic acid amides as detergent additives in lubricating oils.

Udding et al., U.S. Pat. No. 5,468,891 describes antifriction additives for lubricating oils comprising a molybdenum-containing complex prepared by reacting an alkaline earth metal salt of a carboxylic acid, an amine and a source of cationic molybdenum, wherein the ratio of the number of equivalents of acid groups to the number of moles of molybdenum (eq:mol) is in the range from 1:10 to 10:1, and the ratio of the number of equivalents of acid groups to the number of moles of amine (eq:mol) is in the range from 20:1 to 1:10.

Ruhe, Jr. et al., U.S. Pat. No. 6,962,896 describes antioxidant additives for lubricating oils comprising low color molybdenum compounds and polyamide dispersants including molybdenum oxysulfide polyamides.

Gatto et al., U.S. Pat. No. 6,174,842 discloses a lubricating oil composition comprising a lubricating oil, an oil-soluble molybdenum compound substantially free of reactive sulfur, an oil-soluble diarylamine and a calcium phenate as an antiwear and anti-oxidant additive.

John et al., U.S. Pat. No. 7,309,680 discloses a process of reacting in a polar medium an oil soluble or oil dispersible thiomolybdate salt with an ammonium sulfide compound.

Many molybdenum technologies that appear in the patent literature deliver high levels of color when used even at moderate levels in crankcase oils. A non-discoloring molybdenum source is important because highly colored oils imply to the end consumer that the oil is "used" and therefore not capable of delivering the maximum amount of protection to the engine. When these highly colored molybdenum sources are used at low levels, e.g. 100-150 ppm delivered molybdenum as is typically required for oxidation, deposit and wear control, discoloration is not substantial but may still be visible. However, when these highly colored molybdenum compounds are used at high levels, e.g. 400-1000 ppm (or higher) delivered molybdenum as is generally required for friction modification, discoloration is often significant. Traditionally, the color of fully formulated crankcase oils has been determined using the ASTM D 6045 color scale. The amount of acceptable finished lubricant darkening depends on the customer and application. While there are no set standards for the amount of discoloration or darkening that is allowed; certain customers may find it difficult to market and sell such dark crankcase oils. Moreover, many of the molybdenum technologies that appear in the patent literature contain sulfur which can further lead to discoloration. Some forms of sulfur can also be detrimental and corrosive to copper, however sulfur incorporation can have beneficial properties such as antiwear functions of serve as friction modifiers when employed in finished lubricants. Accordingly one aspect of the present invention is directed to the preparation of a sulfurized molybdenum complex having improved color and sulfur functionality while treating the complex with compounds to mitigate the active sulfur detriments.

SUMMARY OF THE INVENTION

The invention is directed to oil soluble additive compositions and lubricating oil compositions derived from a process for preparing a sulfurized oil soluble molybdenum complex having reduced active sulfur comprising: reacting an acidic molybdenum compound with an amide derived from a carboxylic acid component an polyamine component in a ratio from 2:1 to 1:1; thereafter sulfurizing to provide a sulfurized oil soluble molybdenum which is subsequently treated with at least one compound capable of reacting with the active sulfur of step b).

Accordingly, an aspect of the present invention is directed to a process for preparing a sulfurized oil soluble molybdenum complex having reduced active sulfur comprising:

a. reacting an acidic molybdenum compound with a basic nitrogen derived from an amide reaction product of a $C_{4-40}$ aliphatic carboxylic acid component and a polyamine having 2 to 10 nitrogen atoms; wherein the charge mole ratio of the carboxylic acid component to the polyamine component is about 2:1 to 1:1:

b. reacting the product of step a) with a sulfur-containing compound in amounts to provide a sulfurized oil soluble molybdenum complex having 1 to 4 moles of sulfur per mole of molybdenum and active sulfur; and c. reacting the product of step b) with at least one compound capable of reacting with the active sulfur of step b) to thereby reduce the active sulfur in the product of step b).

The charge mole ratio CMR of the carboxylic acid component to the polyamine component can influence the friction reducing properties; accordingly one aspect is directed to a CMR of about 1.7:1 to 1:1. In another aspect, the CMR is 1.7:1 to 1.3:1. In one aspect the polyamine is ethylenediamine or a polyalkylene polyamine and more preferably a polyethylene polyamine which would include tetraethylenepentamine, diethylenetriamine, and ethylenediamine. The reactants and CMR are selected so that there about 0.2 to 1, more preferably from 0.2 to 0.7, and even more preferably 0.4 to 0.7 atoms of molybdenum are present per basic nitrogen atom. In another embodiment the reactants and CMR are selected so that there about 0.2 to 1 atoms of molybdenum are present per basic nitrogen atom. The amide is conveniently prepared by the reaction product of a monocarboxylic fatty acid (particularly isostearic acid, stearic acid, lauric acid, myrstic acid and palmitic acid, and even more preferably isostearic acid and stearic acid) with the polyalkylene amine. Particularly a polyamide of isostearic and tetraethylenepentamine, diethylenetriamine, and ethylenediamine having a CMR of 1.7:1 to 1.3:1.

In one aspect the acidic molybdenum compound is molybdenum added with the addition of a promoter more preferably water employing an elemental sulfur source. This reaction for convenience is conducted with the addition of a diluent.

An aspect is directed to selecting a suitable compound which is capable of reacting with the active sulfur after completion of step b) and thereafter proceeding under suitable reaction conditions so that the resulting reaction product has a reduced active sulfur. Suitable compounds capable of reacting with the active sulfur in step c) are selected from at least one halogen-free inorganic salt; at least one unsaturated compound; at least one hydrocarbyl phosphite; at least one basic nitrogen-containing compound; and mixtures thereof. In one aspect the basic nitrogen-containing compound is selected from the group consisting of at least one amine or amide. In a further aspect, the at least one basic nitrogen-containing compound is an amide selected from the reaction product of at least one fatty acid with at least one polyalkylene polyamine. In one aspect the halogen fee inorganic salt is an alkali metal salt, more particularly a sodium sulfide aqueous solution which after reaction is separated from the organic phase. In one aspect at least one unsaturated compound is a terminal monoolefinic aliphatic hydrocarbon having 8 to 36 carbon atoms. In another aspect the compound capable of reacting with the active sulfur is an unsaturated fatty acid derivative selected from unsaturated fatty acid amide or unsaturated fatty acid amine having from 8 to 22 atoms in the unsaturated fatty acid; with oleyl amine being particularly preferred. In another aspect the compound capable of reacting with the active sulfur in step c) is selected from the reaction product of at least one carboxylic acid with a polyalkylene polyamine; particularly a polyamide of isostearic and tetraethylenepentamine, diethylenetriamine, and ethylenediamine; and even more particularly is directed to a polyamide of isostearic acid and diethylenetriamine. In another aspect, the same amide reaction product is used that is employed in step a) is additionally employed in step c).

Another aspect of the present invention is directed to a lubricating composition comprising a major amount of an oil of lubricating viscosity and a minor amount of the product prepared by the process used for preparing a sulfurized oil soluble molybdenum complex having reduced active sulfur comprising:

a. reacting an acidic molybdenum compound with a basic nitrogen derived from an amide reaction product of a $C_{4-40}$ aliphatic carboxylic acid component and a polyamine having 2 to 10 nitrogen atoms; wherein the charge mole ratio of the carboxylic acid component to the polyamine component is about 2:1 to 1:1:

b. reacting the product of step a) with a sulfur-containing compound in amounts to provide a sulfurized oil soluble molybdenum complex having 1 to 4 moles of sulfur per mole of molybdenum and active sulfur; and c. reacting the product of step b) with at least one compound capable of reacting with the active sulfur of step b) to thereby reduce the active sulfur in the product of step b).

In formulated lubricating oil compositions which further contain at least one additive selected from dispersants, detergents, antioxidants etc, the sulfurized oil soluble molybdenum complex can be added from about 50 ppm to 5000 ppm molybdenum content based on the total formulated lubricating oil composition.

DETAILED DESCRIPTION OF THE INVENTION

While the invention is susceptible to various modifications and alternative forms, specific embodiments thereof and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

Definitions

The following terms will be used throughout the specification and will have the following meanings unless otherwise indicated.

The term "polyamines" refers to organic compounds containing more than one basic nitrogen. The organic portion of the compound may contain aliphatic, cyclic, or aromatic carbon atoms.

The term "polyalkyleneamines" or "polyalkylenepolyamines" refers to compounds represented by the general formula

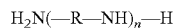

$$H_2N(-R-NH)_n-H$$

wherein R is an alkylene group of preferably 2-3 carbon atoms and n is an integer of from about 1 to 11.

The terms "molybdenum oxide," "molybdenum sulfide," and "molybdenum oxysulfide" refer to compounds of the general formula $MoO_xS_y$, wherein $x \geq 0$, $y \geq 0$, and $12 \geq (x+y) \geq 2$.

The term "carboxylic acid component" refers to carboxylic acids, carboxylates, carboxylic anhydrides, and the esters of carboxylic acids.

The term "fatty acid" refers to a carboxylic acid component derived from or contained in an animal or vegetable fat or oil comprising an alkyl chain of from 4 to 22 carbon atoms with a terminal carboxyl group.

The term "active sulfur" refers to sulfur species present or produced in the sulfurization step described herein that are not chemically bound to the molybdenum in the sulfurized oil-soluble molybdenum complex and which exhibits detrimental effects such as corrosion or elastomer seal incompatibility. Active sulfur is not part of the molybdenum compound itself, but is left behind from the preparation of the molybdenum compound. Active sulfur is also referred to as corrosive sulfur or seal incompatible sulfur. The term active sulfur is sometimes referred to in the prior art as free sulfur, labile sulfur or elemental sulfur, all of which may also be referred to as "reactive" sulfur. It is believed that active sulfur includes divalent sulfur or oxidizable sulfur.

By "soluble" or "oil-soluble" it is meant that the molybdenum compound is oil-soluble or capable of being solubilized under normal blending or use conditions into the lubrication oil or diluent for the concentrate.

The precise molecular formula of the oil soluble additive composition of the invention comprising the salt of (1) a molybdenum oxide, sulfide, or oxysulfide and (2) an amide are not known with certainty; however, they are believed to be compounds in which molybdenum, whose valences are satisfied with atoms of oxygen and sulfur is either complexed by or the salt of one or more basic nitrogens of the amide used in the preparation of these additives.

Molybdenum Component

The molybdenum component used to prepare the oil soluble additive composition of the present invention is a molybdenum containing compound which is a molybdenum oxide, sulfide, or oxysulfide having the general formula of $MoO_xS_y$, wherein $x \geq 0$, $y \geq$ and $12 \geq (x+y) \geq 2$. The molybdenum component can include molybdenum in any oxidation state. The molybdenum component useful in the preparation of the oil-soluble additive composition of the invention may be derived from molybdenum compounds including, but not limited to, molybdenum hexacarbonyl, molybdic acid, ammonium molybdate, sodium molybdate, potassium molybdate, other alkali metal molybdates, alkaline earth metal molybdates, $MoOCl_4$, $MoO_2Br_2$, and $Mo_2O_3Cl_6$. Other molybdenum components include molybdenum trioxide, ammonium tetrathiomolybdate, and molybdenum disulfide. Preferred molybdenum components are molybdenum trioxide and those components derived from molybdic acid and ammonium molybdate. A more preferred molybdenum component is molybdenum trioxide.

Sulfur Source

When employed, representative sulfur sources for preparing the molybdenum components of the oil soluble additive compositions of this invention include but are not limited to sulfur, hydrogen sulfide, sulfur monochloride, sulfur dichloride, phosphorus pentasulfide, $R_2S_x$ where R is hydrocarbyl, preferably $C_1$-$C_{40}$ alkyl, and x is at least 2, inorganic sulfides and polysulfides such as $(NH_4)_2S_x$, where x is at least 1, thioacetamide, thiourea, and mercaptans of the formula RSH where R is as defined above. Also useful as sulfurizing agents are traditional sulfur-containing antioxidants such as wax sulfides and polysulfides, sulfurized olefins, sulfurized carboxylic acid esters and sulfurized ester-olefins, and sulfurized alkylphenols and the metal salts thereof.

Preferred sulfur sources are sulfur, hydrogen sulfide, phosphorus pentasulfide, $R_2S_x$ where R is hydrocarbyl, preferably $C_1$-$C_{10}$ alkyl, and x is at least 3, mercaptans wherein R is $C_1$-$C_{10}$ alkyl, inorganic sulfides and polysulfides, thioacetamide, and thiourea. Most preferred sulfur sources are sulfur, hydrogen sulfide, phosphorus pentasulfide, and inorganic sulfides and polysulfides.

Amide Component of Step a):

The amides used in the preparation of the oil soluble additive composition of the present invention are the reaction product of a carboxylic acid component and a polyamine component. In the reaction of the carboxylic acid component and the amine component to form the amide, the charge mole ratio of the carboxylic acid component to amine component is about 2:1 to 1:1. Preferably the charge mole ratio of the carboxylic acid component to amine component is about 1.7:1 to 1:1. In another embodiment, the charge mole ratio of the carboxylic acid component to amine component is about 1.5:1 to 1:1. In a further embodiment, the charge mole ratio is from about 1.7:1 to about 1.3:1.

In one embodiment, the amide is derived from 1) an aliphatic carboxylic acid component having from about 4 and 40 carbons and 2) a polyamine component having from about 2 and 10 nitrogens. In a preferred embodiment the carboxylic acid component is isostearic acid and the polyamine component is selected from the group consisting of tetraethylenepentamine, diethylenetriamine, ethylenediamine, and mixtures thereof.

The carboxylic acid component and polyamine component described herein below can be reacted to form amides prior to or during reaction with the molybdenum component. Amide compositions useful in the invention include those disclosed in U.S. Pat. No. 3,405,064, the disclosure of which is hereby incorporated by reference. These compositions are ordinarily prepared by reacting a carboxylic acid, carboxylic acid salt, carboxylic acid anhydride, or carboxylic acid ester having at least 4 to about 40 carbon atoms and, if desired, having pendant aliphatic groups to render the molecule oil soluble, with a polyamine, such as an ethylene diamine, to give an amide. Preferred are those amides prepared from (1) an aliphatic monocarboxylic acid, such as isostearic acid, stearic acid or mixtures thereof and (2) an ethylene polyamine, such as tetraethylenepentamine, diethylenetriamine, ethylene diamine or mixtures thereof. Preferably, the amides useful in this invention will have at least one basic nitrogen as measured by ASTM D2896.

Carboxylic Acid Component

The carboxylic acid component used in the preparation of the oil soluble additive composition of the invention includes aliphatic and aromatic carboxylic acids, carboxylic acid salts, carboxylic acid anhydrides, or carboxylic acid esters having from at least 4 to 100 carbon atoms, preferably from 4 to 60 carbon atoms, more preferred from 4 to 40 carbon atoms, and even more preferred from 10 to 30 carbon atoms. Mixtures of carboxylic acids, carboxylic acid salts, carboxylic anhydrides, and carboxylic acid esters can be used in the preparation of the invention. Preferably, the carboxylic acid component is an aliphatic carboxylic acid. Also suitable are monocarboxylic saturated fatty acids particularly selected from the group consisting of capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic aicd, heptacosylic acid, montanic aicid, nonacosylic acid, and melissic acid. Particularly suited examples of aliphatic carboxylic acids include fatty acids such as isostearic acid, stearic acid, lauric acid, myrstic acid, palmitic acid, and arachidic acid. A particularly preferred carboxylic acid component is isostearic acid.

Polyamine Component

The polyamine component used in the preparation of the oil soluble additive composition of the present invention includes aromatic, cyclic, and aliphatic (linear and branched) polyamines and mixtures thereof. Examples of aromatic polyamines include, but are not limited to, phenylenediamine, 2,2'-diaminodiphenylmethane, 2,4- and 2,6-diaminotoluene, 2,6-diamino-p-xylene, multi-nuclear and condensed aromatic polyamines such as naphthylene-1,4-diamine, benzidine, 2,2'-dichloro-4,4'-diphenyl diamine and 4,4'-diaminoazobenzene. In another embodiment the polyamine component comprises polyamines of from about 5 to 32 ring members and having from about 2 to 8 amine nitrogen atoms. Such polyamine compounds include such compounds as piperazine, 2-methylpiperazine, N-(2-aminoethyl)piperazine, N-(2-hydroxyethyl)piperazine, 1,2-bis-(N-piperazinyl)ethane, 3-aminopyrrolidine, N-(2-aminoethyl)pyrrolidine, and aza crown compounds such as triazacyclononane, tetraazacyclododecane, and the like.

In a preferred embodiment, the polyamine component used in the preparation of this invention are polyalkylenepolyamines and can be represented by the general formula

wherein R is an alkylene group of preferably 2-3 carbon atoms and n is an integer of from 1 to 11 and even more preferably from 2-5.

Specific examples of polyalkylenepolyamines include, but are not limited to, diethylenetriamine, triethylenetetramine, tetraethylenepentamine, pentaethylenehexamine, hexaethyleneheptamine, heptaethyleneoctamine, octaethylenenonamine, nonaethylenedecamine, decaethyleneundecamine, undecaethylenedodecamine, dipropylenetriamine, tripropylenetetramine, tetrapropylenepentamine, pentapropylenehexamine, hexapropyleneheptamine, heptapropyleneoctamine, octapropylenenonamine, nonapropylenedecamine, decapropyleneundecamine, undecapropylenedodecamine, di(trimethylene)triamine, tri(trimethylene)tetramine, tetra(trimethylene)pentamine, penta(triethylene)hexamine, hexa(trimethylene)heptamine, hepta(trimethylene)octamine, octa(trimethylene)nonamine, nona(trimethylene)decamine, deca(trimethylene)undecamine and undeca(trimethylene)dodecamine.

Compound Capable of Reacting with Active Sulfur

The at least one compound capable of reacting with active sulfur include without limitation any compound that is capable of reducing the active sulfur content of the reaction product of step b). In one embodiment the at least one compound capable of reacting with active sulfur is selected from at least one halogen-free inorganic salt; at least one unsaturated compound, especially olefins and unsaturated fatty acids and unsaturated fatty acid derivatives; at least one hydrocarbyl phosphite, especially triphenyl and trialkyl phosphites; at least one basic nitrogen-containing compound, especially ammonia, hydrocarbyl amines and polyamines; and mixtures thereof. Basic nitrogen of the compounds can be measured by ASTM D2896. Particularly preferred basic nitrogen compounds having amide or amine functionality. Mixtures of different compounds capable of reacting with active sulfur may also be employed.

The use of halogen-free inorganic salts to reduce the active sulfur content of reaction products containing active sulfur is disclosed in many documents especially U.S. Pat. Nos. 3,498,915 and 4,119,550. A preferred inorganic salt is especially an inorganic sulfide, especially sodium sulfide. In an exemplary process employing sodium sulfide, treatment involves the mixing together of the sulfurized reaction product and a sodium sulfide solution, typically an aqueous solution containing from about 5 to 75% $Na_2S$, for a period of time sufficient for unreacted sulfur to be scavenged, usually a period of a few minutes to several hours depending on the amount of unreacted sulfur, the quantity and the concentration of the sodium sulfide solution. After the treatment, the resulting aqueous phase is separated from the organic phase by conventional techniques, e.g., decantation, etc. Other alkali metal sulfides may be used to scavenge active sulfur but sodium sulfide solutions are preferred for reasons of economy and effectiveness.

The use of unsaturated compounds to reduce the active sulfur content of reaction products containing active sulfur is disclosed in many documents, in particular U.S. Pat. No. 4,289,635. In one embodiment the unsaturated compound contains at least one non-aromatic double bond; that is, one connecting two aliphatic carbon atoms. The natures of other substituents in the unsaturated compound are not normally a critical aspect of the invention, and any such substituent is useful so long as it is or can be made compatible with lubricating environments and does not interfere under the contemplated reaction conditions. Thus, substituted compounds which are so unstable as to deleteriously decompose under the reaction conditions employed are not contemplated. However, certain substituents such as keto or aldehydro can desirably undergo sulfurization. The selection of suitable substituents is within the skill of the art or may be established through routine testing. Typical of such substituents include any of the above-listed moieties as well as hydroxy, amidine, amino, sulfonyl, sulfinyl, sulfonate, nitro, phosphate, phosphite, alkali metal mercapto and the like. In one embodiment the unsaturated compound is ashless.

In one embodiment the at least one unsaturated compound is at least one hydrocarbon containing at least one non-aromatic double bond. In another embodiment the unsaturated compound is an olefin, i.e. an aliphatic hydrocarbon containing at least one non-aromatic double bond. Monoolefinic and diolefinic compounds, particularly the former, are preferred, and especially terminal monoolefinic aliphatic hydrocarbons (i.e. alpha-olefins). Olefinic compounds having from about 8 up to about 36 and especially from about 8 up to about 20 carbon atoms are particularly desirable. In one embodiment the unsaturated compound is a linear alpha-olefin. Alpha-olefins and mixtures of alpha-olefins are commercially available and such mixtures are suitable for use in this invention.

In another embodiment the unsaturated compound is at least one unsaturated fatty acid or fatty acid derivative, such as an unsaturated fatty acid amide, unsaturated fatty acid amine, or unsaturated fatty acid ester. Suitable fatty acids may be obtained by hydrolysis of a naturally occurring vegetable or animal fat or oil. These are usually in the 8 to 22 carbon range, especially the 16 to 20 carbon range, and include oleic acid, linoleic acid and the like.

Fatty acid esters which are useful are primarily esters of aliphatic alcohols, including monohydric alcohols such as methanol, ethanol, n-propanol, isopropanol, the butanols, etc., and polyhydric alcohols including ethylene glycol, propylene glycol, trimethylene glycol, neopentyl glycol, glycerol and the like. Particularly preferred are fatty oils derived predominantly from unsaturated acids, that is, naturally occurring triglycerides of long chain unsaturated carboxylic acids, especially linoleic and oleic acids. These fatty oils include such naturally occurring animal and vegetable oils as lard oil, peanut oil, cotton seed oil, soybean oil, corn oil and the like.

Unsaturated fatty acid amides can be derived from the condensation reaction of unsaturated fatty acids and at least one amine, or ammonia. In one embodiment the unsaturated fatty acid amide is the reaction product of an unsaturated fatty acid and ammonia, e.g. oleyl amide. In another embodiment the unsaturated fatty acid amide is the reaction product of an unsaturated fatty acid and a monoamine In another embodiment the unsaturated fatty acid amide is the reaction product of an unsaturated fatty acid and a polyamine, such as a polyalkylene polyamine.

Unsaturated fatty amines can be prepared via the product of aminating at least one unsaturated fatty acid with ammonia or a polyamine, such as a polyalkylene polyamine. A preferred unsaturated fatty amine is oleyl amine.

In one embodiment the at least one unsaturated fatty acid or fatty acid derivative is at least one unsaturated fatty acid amide or unsaturated fatty acid amine. As will be disclosed below, the use of at least one unsaturated fatty acid amide or unsaturated fatty acid amine has the added benefit of reducing active sulfur through reaction with the basic nitrogen functionality as well as with the unsaturation.

The use of at least one hydrocarbyl phosphite to reduce the active sulfur content of reaction products containing active sulfur is disclosed in for example U.S. Pat. No. 4,263,150. In one embodiment the hydrocarbyl phosphite has the formula $(R'O)_3P$, wherein each $R'$ is a hydrocarbon-based radical or hydrogen, and no more than one $R'$ is hydrogen. In one embodiment $R'$ is hydrogen or up to seven carbon hydrocarbyl. In another embodiment $R'$ is up to $C_{18}$ aryl and especially phenyl. As is apparent from the definition of the phosphite herein, it may be tertiary or secondary. That is, it may contain three or only two (respectively) hydrocarbon-based radicals per molecule. In one embodiment the hydrocarbyl phosphite is at least one tertiary phosphite. In one embodiment the at least one hydrocarbyl phosphite is triphenyl phosphite. Mixtures of such hydrocarbyl phosphites can also be used.

The at least one basic nitrogen-containing compound must have a basic nitrogen content of greater than zero when titrated by ASTM D 2896. In one embodiment the at least one basic nitrogen-containing compound useful in this invention is at least one amine or amide. In one embodiment the at least one basic nitrogen-containing compound useful in this invention is at least one amine. The use of at least one amine to reduce the active sulfur content of reaction products containing active sulfur is disclosed in for example EP 395258. Amines useful in the invention include saturated or unsaturated hydrocarbyl amines represented by the formula $HNR_3R_4$, where $R_3$ can be hydrogen and $R_3$ and $R_4$ can be independently selected from alkyl, cycloalkyl, or alkenyl radicals, including substituted moieties thereof substituted with non-hydrocarbon substituents which do not alter the predominantly hydrocarbon character of the groups such as halo, hydroxy, nitro, cyano, alkoxy, or acyl, having 1 to 30 carbon atoms. Preferred are primary alkyl or alkenyl amines having 4 to 22 carbon atoms such as, for example, n-butylamine, n-hexylamine, n-octylamine, n-dodecylamine, n-octadecylamine, oleylamine, 2-ethyl-n-hexylamine, t-butylamine, and t-octylamine. Mixtures of such amines as well as commercially available mixed amines can also be used such as those derived from natural products, e.g., cocoamine and tallow amine, which comprise various mixtures of amines containing from 12 to 22 carbon atoms, i.e. $C_{12-14}$, $C_{16-18}$ and $C_{16-22}$ mixtures thereof. Cycloalkyl amines preferably have 4 to 6 carbon atoms in the ring. Examples of such compounds include cyclohexylamine, aminomethylcyclohexane, cyclobutyl amine, and cyclopentyl amine.

In one embodiment the at least one basic nitrogen-containing compound useful in this invention is at least one amide. In one embodiment the at least one amide is the residue of the reaction of at least one carboxylic acid, such as at least one fatty acid, with at least one polyamine, such as at least one polyethylene polyamine. Suitable amides have been described in the amide component of step a) which are suitable for use herein. In one embodiment the amide is the product obtainable by reacting at least one fatty acid with at least one polyalkylene polyamine. In one embodiment the amide is the reaction product of isostearic acid and diethylenetriamine (DETA).

In one embodiment at least one compound capable of reacting with active sulfur is at least one oil soluble compound. The advantage to using oil soluble compounds is that further separation steps are not necessary. In one embodiment the at least one oil soluble compound capable of reacting with active sulfur is selected from at least one unsaturated compound; at least one hydrocarbyl phosphite; at least one basic nitrogen-containing compound; and mixtures thereof.

Method for Making the Oil Soluble Composition of the Present Invention

The preparation of this invention may be carried out by combining the molybdenum component and the amide component of step a). A polar promoter can be optionally added to the reaction mixture. The amide component can be formed prior to reaction with the molybdenum component or in situ from a carboxylic acid component and a polyamine component. Typically more for convenience, and to more particularly control the charge mole ratios, the amide component is formed prior to the molybdenum addition. Preferably, the reaction product of the molybdenum component and the amide is sulfurized by reacting with a sulfur component. The preparation of this invention may be carried out by combining the molybdenum component with the sulfur component to form a molybdenum sulfide or oxysulfide prior to addition of the amide component. In a preferred embodiment, the molybdenum component and the amide are reacted to form a salt of a molybdenum oxide and an amide followed by sulfurization with a sulfur component to form the salt of a molybdenum sulfide or oxysulfide and an amide. The order of addition of the reaction components is not critical. The reaction is ordinarily carried out at atmospheric pressure; however, higher or lower pressures may be used, if desired, using methods that are well-known to those skilled in the art. A diluent may be used to enable the reaction mixture to be efficiently stirred. Typical diluents are lubricating oil and liquid compounds containing only carbon and hydrogen. If the mixture is sufficiently fluid to permit satisfactory mixing, no diluent is necessary. A diluent which does not react with the molybdenum component is desirable.

Optionally, a polar promoter may be employed in the preparation of the present invention. The polar promoter facilitates the interaction between the molybdenum component and the basic nitrogen of the polyamine or amide component. A wide variety of such promoters may be used. Typical promoters are 1,3-propanediol, 1,4-butanediol, diethylene glycol, butyl cellosolve, propylene glycol, 1,4-butylenegly-col, methyl carbitol, ethanolamine, diethanolamine, N-methyl-diethanol-amine, dimethyl formamide, N-methyl acetamide, dimethyl acetamide, ammonium hydroxides, tetraalkyl ammonium hydroxides, alkali metal hydroxides, methanol, ethylene glycol, dimethyl sulfoxide, hexamethyl phosphoramide, tetrahydrofuran, acetic acid, inorganic acids, and water. Preferred are water and ethylene glycol. Particularly preferred is water.

While ordinarily the polar promoter is separately added to the reaction mixture, it may also be present, particularly in the case of water, as a component of non-anhydrous starting materials or as waters of hydration in the molybdenum component, such as $(NH_4)_6Mo_7O_{24} \cdot 4H_2O$. Water may also be added as ammonium hydroxide.

A general method for preparing the oil soluble additive compositions of this invention comprises step a): reacting (1) a molybdenum component and (2) an amide of a carboxylic acid and a polyamine in which the carboxylic acid and polyamine have a charge mole ratio (CMR) of between about 2:1 to 1:1. Optionally, (3) a polar promoter or (4) a diluent, to form a salt or (5) both a polar promoter and a diluent may be added. The diluent is used, if necessary, to provide a suitable viscosity to facilitate mixing and handling. Typical diluents are lubricating oil and liquid compounds containing only carbon and hydrogen. Optionally, ammonium hydroxide may also be added to the reaction mixture to provide a solution of ammonium molybdate. The molybdenum component, amide, polar promoter, if used, and diluent, if used, are charged to a reactor and heated at a temperature less than or equal to about 200° C., preferably from about 70° C. to about 120° C. The temperature is maintained at a temperature less than or equal to about 200° C., preferably at about 70° C. to about 90° C., until the molybdenum component is sufficiently reacted. The reaction time for this step is typically in the range of from about 1 to about 30 hours and preferably from about 1 to about 10 hours.

The reaction mixture is further reacted in step b), with a sulfur component as defined above, at a suitable pressure and temperature not to exceed 200° C. The sulfurization step is typically carried out for a period of from about 0.5 to about 5 hours and preferably from about 0.5 to about 2 hours. In some cases, removal of the polar promoter from the reaction mixture may be desirable prior to completion of reaction with the sulfur component.

The sulfur component is usually charged to the reaction mixture in such a ratio to provide up to 12 atoms of sulfur per atom of molybdenum. In one embodiment, the oil soluble composition of the invention will have a mole ratio of molybdenum to sulfur of 1:0 to 1:8. In another embodiment the mole ratio of molybdenum to sulfur is from about 1:0 to 1:4. In a further embodiment, the mole ratio of molybdenum to sulfur is from about 1:1 to 1:4. In a further embodiment, the mole ratio of molybdenum to sulfur is from about 1:1 to 1:3. In a further embodiment, the mole ratio of molybdenum to sulfur is from about 1:1 to 1:2.

In the reaction mixture the ratio of molybdenum atoms to basic nitrogen atoms provided by the amide can range from about 0.01 to 4.0 atoms of molybdenum per basic nitrogen atom. Usually the reaction mixture is charged from 0.01 to 2.00 atoms of molybdenum per basic nitrogen atom provided by the amide. Preferably from 0.4 to 1.0, and most preferably from 0.4 to 0.7, atoms of molybdenum per atom of basic nitrogen are added to the reaction mixture. In another embodiment from 0.2 to 1.0, and more preferably from 0.2 to 0.7, atoms of molybdenum per atom of basic nitrogen are added to the reaction mixture.

The polar promoter, which is preferably water, is ordinarily present in the ratio of 0.1 to 50 moles of water per mol of molybdenum. Preferably from 0.5 to 25 and most preferably 1.0 to 15 moles of the promoter is present per mole of molybdenum.

The charge mole ratio of the carboxylic acid component to polyamine is critical and can range from about 2:1 to 1:1. In one embodiment the charge mole ratio is from about 1.7:1 to 1:1. In another embodiment the charge mole ratio is from about 1.5:1 to 1:1. In a further embodiment the charge mole ratio is from about 1.7:1 to 1.3:1. The amide formed from the reaction of the carboxylic acid component and the polyamine may occur prior to, during, or after the introduction of the molybdenum component to the reaction mixture.

The reaction product of step b) is further reacted in step c) with at least one compound capable of reacting with the active sulfur contained in the reaction product of step b). Active sulfur particularly affects yellow metal components of engines, gears and other components exposed to the lubricating oil compositions containing active sulfur; and more specifically, the copper and copper alloys component parts. The detrimental effects of active sulfur are commonly measured by the ASTM D130 test method which was developed to measure the stability of a lubricating oil in the presence of copper and copper alloys or more particularly the extent of copper corrosion. In one embodiment step c) of the invention is conducted under suitable conditions and amounts to provide an ASTM D130 corrosion test result of 3B or better, more preferably 2B or better, even more preferably 1B or better, most preferably 1A when the final reaction product is used in a finished lubricant. Reacting at least a portion of the active sulfur from the reaction product of step b) with at least one compound capable of reacting with the active sulfur has been discovered to show improved copper corrosion performance, improved viscometric properties and improved color attributes in the final reaction product.

In step c) the suitable compound which may react with the active sulfur contained in the reaction product of step b) constitutes from 0.01 to 25 weight percent based upon the product of step b), more preferably from 1 to 15 weight percent and even more preferably the compound constitutes from 3 to 10 weight percent of the product of step b). The product of step b) and the at least one compound capable of reacting with the active sulfur of step b) are charged to a reactor and heated to a temperature suitable for reaction. Typically this reaction temperature is less than or equal to about 200° C., preferably from 50° C. to 180° C. In another embodiment the reaction temperature is from 70° C. to 150° C. In a further embodiment, the reaction temperature is from 100° C. to 140° C.

In step c), the period of time for reaction of the product of step b) and at least one compound capable of reacting with the active sulfur varies with several factors including nature and amount of reactants, reaction equipment, solvent/diluent medium, degree of mixing, and the like. The reaction time should be long enough to complete the desired reduction in the active sulfur content. In one embodiment the period of time for reaction in step c) is from 0.5 to 20 hours. In one embodiment the period of time for reaction in step c) is from 0.5 to 10 hours. In one embodiment the period of time for reaction in step c) is from 1 to 5 hours. In another embodiment the period of time is from 2 to 15 hours or may be conducted typically within from 5 to 10 hours.

It is preferred to carry out the reaction of step c) while sparging the reaction mixture an oxygen-containing gas such as air. Sparging with an oxygen-containing gas enhances the reduction of active sulfur. If the oxygen containing gas is applied, it should be distributed evenly throughout the reactor by a proper gas distributor.

Typically at the end of the reaction, excess water and any volatile diluents are removed from the reaction mixture. Removal methods include, but are not limited to, vacuum distillation or nitrogen stripping while maintaining the temperature of the reactor at a temperature less than or equal to about 200° C., preferably between about 70° C. to about 90° C. In another embodiment the temperature of the stripping step is 100° C. to 180° C. In another embodiment the temperature of the stripping step is 100° C. to 150° C. In another embodiment the temperature of the stripping step is 90° C. to 180° C. The removal of water and volatile diluents is ordinarily carried out under reduced pressure. The pressure may be reduced incrementally to avoid problems with foaming. After the desired pressure is reached, the stripping step is typically carried out for a period of about 0.5 to about 5 hours and preferably from about 0.5 to about 2 hours.

Additive Concentrates

In many instances, it may be advantageous to form concentrates of the oil soluble additive composition of the present invention within a carrier liquid. These additive concentrates provide a convenient method of handling, transporting, and ultimately blending into lubricant base oils to provide a finished lubricant. Generally, the oil soluble additive concentrates of the invention are not useable or suitable as finished lubricants on their own. Rather, the oil soluble additive concentrates are blended with lubricant base oil stocks to provide a finished lubricant. It is desired that the carrier liquid readily solubilizes the oil soluble additive of the invention and provides an oil additive concentrate that is readily soluble in the lubricant base oil stocks. In addition, it is desired that the carrier liquid not introduce any undesirable characteristics, including, for example, high volatility, high viscosity, and impurities such as heteroatoms, to the lubricant base oil stocks and thus, ultimately to the finished lubricant. The present invention therefore further provides an oil soluble additive concentrate composition comprising an inert carrier fluid and from 2.0% to 90% by weight, based on the total concentrate, of an oil soluble additive composition according to the invention. The inert carrier fluid may be a lubricating oil.

These concentrates usually contain from about 2.0% to about 90% by weight, preferably 10% to 50% by weight of the oil soluble additive composition of this invention and may contain, in addition, one or more other additives known in the art and described below. The remainder of the concentrate is the substantially inert carrier liquid.

Lubricating Oil Compositions

In one embodiment of the invention, the oil soluble additive composition of the present invention can be mixed with a base oil of lubricating viscosity to form a lubricating oil composition. The lubricating oil composition comprises a major amount of a base oil of lubricating viscosity and a minor amount of the oil soluble additive composition of the present invention described above.

The lubricating oil which may be used in this invention includes a wide variety of hydrocarbon oils, such as naphthenic bases, paraffin bases and mixed base oils as well as synthetic oils such as esters and the like. The lubricating oils which may be used in this invention also include oils from biomass such as plant and animal derived oils. The lubricating oils may be used individually or in combination and generally have viscosity which ranges from 7 to 3,300 cSt and usually from 20 to 2000 cSt at 40° C. Thus, the base oil can be a refined paraffin type base oil, a refined naphthenic base oil, or a synthetic hydrocarbon or non-hydrocarbon oil of lubricating viscosity. The base oil can also be a mixture of mineral and synthetic oils. Mineral oils for use as the base oil in this invention include, for example, paraffinic, naphthenic and other oils that are ordinarily used in lubricating oil compositions. Synthetic oils include, for example, both hydrocarbon synthetic oils and synthetic esters and mixtures thereof having the desired viscosity. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. Useful synthetic hydrocarbon oils include liquid polymers of alpha olefins having the proper viscosity. Likewise, alkyl benzenes of proper viscosity, such as didodecyl benzene, can be used. Useful synthetic esters include the esters of monocarboxylic acids and polycarboxylic acids, as well as mono-hydroxy alkanols and polyols. Typical examples are didodecyl adipate, pentaerythritol tetracaproate, di-2-ethylhexyl adipate, dilaurylsebacate, and the like. Complex esters prepared from mixtures of mono and dicarboxylic acids and mono and dihydroxy alkanols can also be used. Blends of mineral oils with synthetic oils are also useful.

The lubricating oil compositions containing the oil soluble additives of this invention can be prepared by admixing, by conventional techniques, the appropriate amount of the oil soluble additives of the invention with a lubricating oil. The selection of the particular base oil depends on the contemplated application of the lubricant and the presence of other additives. Generally, the amount of the oil soluble additive of the invention in the lubricating oil composition of the invention will vary from 0.05 to 15% by weight and preferably from 0.2 to 1% by weight, based on the total weight of the lubricating oil composition. In one embodiment, the molybdenum content of the lubricating oil composition will be between about 50 parts per million (ppm) and 5000 ppm, preferably between about 90 ppm to 1500 ppm. In another embodiment the molybdenum content of the lubricating oil composition will be between about 500 ppm and 700 ppm.

Additional Additives

If desired, other additives may be included in the lubricating oil and lubricating oil concentrate compositions of this invention. These additives include antioxidants or oxidation inhibitors, dispersants, rust inhibitors, anticorrosion agents and so forth. Also, anti-foam agents, stabilizers, anti-stain agents, tackiness agents, anti-chatter agents, dropping point improvers, anti-squawk agents, extreme pressure agents, odor control agents and the like may be included.

The following additive components are examples of some of the components that can be favorably employed in the lubricating oil compositions of the present invention. These examples of additional additives are provided to illustrate the present invention, but they are not intended to limit it:

Metal Detergents

Detergents which may be employed in the present invention include alkyl or alkenyl aromatic sulfonates, calcium phenate, borated sulfonates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multiacid, and chemical and physical mixtures thereof.

Anti-Wear Agents

As their name implies, these agents reduce wear of moving metallic parts. Examples of such agents include, but are not limited to, zinc dithiophosphates, carbamates, esters, and molybdenum complexes.

Rust Inhibitors (Anti-Rust Agents)

Anti-rust agents reduce corrosion on materials normally subject to corrosion. Examples of anti-rust agents include, but are not limited to, nonionic polyoxyethylene surface active agents such as polyoxyethylene lauryl ether, polyoxyethylene higher alcohol ether, polyoxyethylene nonyl phenyl ether, polyoxyethylene octyl phenyl ether, polyoxyethylene octyl stearyl ether, polyoxyethylene oleyl ether, polyoxyethylene sorbitol monostearate, polyoxyethylene sorbitol mono-oleate, and polyethylene glycol mono-oleate. Other compounds useful as anti-rust agents include, but are not limited to, stearic acid and other fatty acids, dicarboxylic acids, metal soaps, fatty acid amine salts, metal salts of heavy sulfonic acid, partial carboxylic acid ester of polyhydric alcohol, and phosphoric ester.

Demulsifiers

Demulsifiers are used to aid the separation of an emulsion. Examples of demulsifiers include, but are not limited to, block copolymers of polyethylene glycol and polypropylene glycol, polyethoxylated alkylphenols, polyesteramides, ethoxylated alkylphenol-form aldehyde resins, polyvinylalcohol derivatives and cationic or anionic polyelectrolytes. Mixtures of different types of polymers may also be used.

Friction Modifiers

Additional friction modifiers may be added to the lubricating oil of the present invention. Examples of friction modifiers include, but are not limited to, fatty alcohols, fatty acids, amines, ethoxylated amines, borated esters, other esters, phosphates, phosphites and phosphonates.

Multifunctional Additives

Additives with multiple properties such as anti-oxidant and anti-wear properties may also be added to the lubricating oil of the present invention. Examples of multi-functional additives include, but are not limited to, sulfurized oxymolybdenum dithiocarbamate, sulfurized oxymolybdenum organo phosphorodithioate, oxymolybdenum monoglyceride, oxymolybdenum diethylate amide, amine-molybdenum complexes, and sulfur-containing molybdenum complexes.

Viscosity Index Improvers

Viscosity index improvers, also known as viscosity modifiers, comprise a class of additives that improve the viscosity-temperature characteristics of the lubricating oil, making the oil's viscosity more stable as its temperature changes. Viscosity index improvers may be added to the lubricating oil composition of the present invention. Examples of viscosity index improvers include, but are not limited to, polymethacrylate type polymers, ethylene-propylene copolymers, styrene-isoprene copolymers, alkaline earth metal salts of phosphosulfurized polyisobutylene, hydrated styrene-isoprene copolymers, polyisobutylene, and dispersant type viscosity index improvers.

Pour Point Depressants

Pour point depressants are polymers that are designed to control wax crystal formation in lubricating oils resulting in lower pour point and improved low temperature flow performance. Examples of pour point depressants include, but are not limited to, polymethyl methacrylate, ethylene vinyl acetate copolymers, polyethylene polymers, and alkylated polystyrenes.

Foam Inhibitors

Foam inhibitors are used to reduce the foaming tendencies of the lubricating oil. Examples of foam inhibitors include, but are not limited to, alkyl methacrylate polymers, alkylacrylate copolymers, and polymeric organosiloxanes such as dimethylsiloxane polymers.

Metal Deactivators

Metal deactivators create a film on metal surfaces to prevent the metal from causing the oil to be oxidized. Examples of metal deactivators include, but are not limited to, disalicylidene propylenediamine, triazole derivatives, thiadiazole derivatives, bis-imidazole ethers, and mercaptobenzimidazoles.

Dispersants

Dispersants diffuse sludge, carbon, soot, oxidation products, and other deposit precursors to prevent them from coagulating resulting in reduced deposit formation, less oil oxidation, and less viscosity increase. Examples of dispersants include, but are not limited to, alkenyl succinimides, alkenyl succinimides modified with other organic compounds, alkenyl succinimides modified by post-treatment with ethylene carbonate or boric acid, alkali metal or mixed alkali metal, alkaline earth metal borates, dispersions of hydrated alkali metal borates, dispersions of alkaline-earth metal borates, polyamide ashless dispersants and the like or mixtures of such dispersants.

Anti-Oxidants

Anti-oxidants reduce the tendency of mineral oils to deteriorate by inhibiting the formation of oxidation products such as sludge and varnish-like deposits on the metal surfaces. Examples of anti-oxidants useful in the present invention include, but are not limited to, phenol type (phenolic) oxidation inhibitors, such as 4,4'-methylene-bis(2,6-di-tert-butylphenol), 4,4'-bis(2,6-di-tert-butylphenol), 4,4'-bis(2-methyl-6-tert-butylphenol), 2,2'-methylene-bis(4-methyl-6-tert-butylphenol), 4,4'-butylidene-bis(3-methyl-6-tert-butylphenol), 4,4'-isopropylidene-bis(2,6-di-tert-butylphenol), 2,2'-methylene-bis(4-methyl-6-nonylphenol), 2,2'-isobutylidene-bis(4,6-dimethylphenol), 2,2'-5-methylene-bis(4-methyl-6-cyclohexylphenol), 2,6-di-tert-butyl-4-methylphenol, 2,6-di-tert-butyl-4-ethylphenol, 2,4-dimethyl-6-tert-butyl-phenol, 2,6-di-tert-1-dimethylamino-p-cresol, 2,6-di-tert-4-(N,N'-dimethylaminomethylphenol), 4,4'-thiobis(2-methyl-6-tert-butylphenol), 2,2'-thiobis(4-methyl-6-tert-butylphenol), bis(3-methyl-4-hydroxy-5-tert-10-butylbenzyl)-sulfide, and bis(3,5-di-tert-butyl-4-hydroxybenzyl). Diphenylamine-type oxidation inhibitors include, but are not limited to, alkylated diphenylamine, phenyl-alpha-naphthylamine, and alkylated-alpha-naphthylamine. Other types of oxidation inhibitors include metal dithiocarbamate (e.g., zinc dithiocarbamate), and methylenebis (dibutyldithiocarbamate).

Applications

Lubricating oil compositions containing the oil soluble additive compositions disclosed herein are effective as either fluid and grease compositions for modifying the friction properties of the lubricating oil which may, when used as a crankcase lubricant, lead to improved mileage for the vehicle being lubricated with a lubricating oil of this invention.

The lubricating oil compositions of this invention may be used in marine cylinder lubricants as in crosshead diesel engines, crankcase lubricants as in automobiles and railroads, lubricants for heavy machinery such as steel mills and the like, or as greases for bearings and the like. Whether the lubricant is fluid or solid will ordinarily depend on whether a thickening agent is present. Typical thickening agents include polyurea acetates, lithium stearate and the like. The oil soluble additive composition of the invention may also find utility as an anti-oxidant, anti-wear additive in explosive emulsion formulations.

Additional Applications

The oil soluble additive compositions of the invention can be envisioned as hydrotreating catalyst precursors in addition to their use as lubricating oil additives. The oil soluble additive compositions of the invention can act as a catalyst precursor and can be contacted with hydrocarbons and decomposed, in the presence of hydrogen and sulfur or sulfur-bearing compounds to form an active catalyst for hydrotreating a hydrocarbonaceous feedstock. The oil soluble additive compositions of the invention can be heated to the decomposition temperature and decomposed in the presence of hydrogen a hydrocarbon, and sulfur or sulfur-bearing compounds, e.g., at "on-oil" conditions, to form the active catalyst species for hydrotreating.

The nature of the hydrocarbon is not critical, and can generally include any hydrocarbon compound, acyclic or cyclic, saturated or unsaturated, unsubstituted or inertly substituted. The preferred hydrocarbons are those which are liquid at ordinary temperatures, exemplary of which are such straight chain saturated acyclic hydrocarbons as octane, tridecane, eicosane, nonacosane, or the like; straight chain unsaturated acyclic hydrocarbons as 2-hexene, 1,4-hexadiene, and the like; branched chain saturated acyclic hydrocarbons as 3-methylpentane, neopentane, isohexane, 2,7,8-triethyldecane, and the like; branched chain unsaturated acyclic hydrocarbons such as 3,4-dipropyl-1,3-hexadiene-5-yne, 5,5-dimethyl-1-hexene, and the like; cyclic hydrocarbons, saturated or unsaturated, such as cyclohexane, 1,3-cyclohexadiene, and the like; and including such aromatics as cumene, mesitylene, styrene, toluene, o-xylene, or the like. The more preferred hydrocarbons are those derived from petroleum, including especially admixtures of petroleum hydrocarbons characterized as virgin naphthas, cracked naphthas, Fischer-Tropsch naphtha, light cycle oil, medium cycle oil, heavy cycle oil, and the like, typically those containing from about 5 to about 30 carbon atoms, preferably from about 5 to about 20 carbon atoms and boiling within a range of from about 30° C. to about 450° C., preferably from about 150° C. to about 300° C. In decomposing the oil soluble additive compositions of the invention to form a hydrotreating catalyst, a packed bed containing the oil soluble additive compositions of the invention is contacted in a hydrogen atmosphere with both the hydrocarbon and sulfur or sulfur-bearing compound and heated at conditions which decompose said oil soluble additive compositions of the invention.

The sulfur or sulfur-bearing compound is characterized as an organo-sulfur or hydrocarbyl-sulfur compound, which contains one or more carbon-sulfur bonds within the total molecule, and generally includes acyclic or cyclic, saturated or unsaturated, substituted or inertly substituted compounds. Exemplary of acyclic compounds of this character are ethyl sulfide, n-butyl sulfide, n-hexylthiol, diethylsulfone, allyl isothiocyanate, dimethyl disulfide, ethylmethylsulfone, ethylmethylsulfoxide, and the like; cyclic compounds of such character are methylthiophenol, dimethylthiophene, 4-mercaptobenzoic acid, benzenesulfonic acid, 5-formamido-benzothiazole, 1-naphthalenesulfonic acid, dibenzylthiophene, and the like. The sulfur must be present in at least an amount sufficient to provide the desired stoichiometry required for the catalyst, and preferably is employed in excess of this amount. Suitably, both the hydrocarbon and sulfur for the reaction can be supplied by the use of a sulfur-containing hydrocarbon compound, e.g., a heterocyclic sulfur compound, or compounds. Exemplary of heterocyclic sulfur compounds suitable for such purpose are thiophene, dibenzothiophene, tetraphenylthiophene, tetramethyldibenzothiophene, tetrahydrodibenzothiophene, thianthrene, tetramethylthianthrene, and the like. The hydrogen required for forming the catalysts of this invention may be pure hydrogen, an admixture of gases rich in hydrogen or a compound which will generate in situ hydrogen, e.g., a hydrogen-generating gas such as carbon monoxide mixtures with water, or a hydrogen donor solvent.

Excellent friction reducing properties have been demonstrated for the salts of (1) molybdenum oxides, sulfides, or oxysulfides and (2) an amide reaction product of a carboxylic acid component and a polyamine component wherein the charge mole ratio (CMR) of the carboxylic acid component to the polyamine component is from about 2:1 to about 1:1. This aspect can be directed to an oil soluble additive composition comprising the salt of:
(1) a molybdenum component which is a molybdenum oxide, sulfide, or oxysulfide of the general formula $MoO_xS_y$, wherein $x \geq 0$, $y \geq 0$, and $12 \geq (x+y) \geq 2$; and
(2) an amide wherein said amide comprises the reaction product of a carboxylic acid component and a polyamine component, wherein the charge mole ratio of the carboxylic acid component to the polyamine component is about 2:1 to 1:1. Another aspect can be directed to a lubricating oil composition comprising:
(1) an oil of lubricating viscosity and
(2) an oil soluble additive composition comprising the salt of:
  (a) a molybdenum component which is a molybdenum oxide, sulfide, or oxysulfide of the general formula $MoO_xS_y$, wherein $x \geq 0$, $y \geq 0$, and $12 \geq (x+y) \geq 2$; and
  (b) an amide wherein said amide comprises the reaction product of a carboxylic acid component and a polyamine component, wherein the charge mole ratio of the carboxylic acid component to the polyamine component is about 2:1 to 1:1.

An aspect can be directed to a lubricating oil concentrate composition comprising:
(1) an oil of lubricating viscosity and
(2) from about 2.0 wt % to about 90 wt % of an oil soluble additive composition comprising the salt of
  (a) a molybdenum component which is a molybdenum oxide, sulfide, or oxysulfide of the general formula $MoO_xS_y$, wherein $x \geq 0$, $y \geq 0$, and $12 \geq (x+y) \geq 2$; and
  (b) an amide wherein said amide comprises the reaction product of a carboxylic acid component and a polyamine component, wherein the charge mole ratio of the carboxylic acid component to the polyamine component is about 2:1 to 1:1.

The above aspects can be manufactured according to the process for preparing an oil soluble composition which comprises reacting:
(1) a molybdenum component which is, or is capable of forming, a molybdenum oxide, sulfide, or oxysulfide; and
(2) an amide wherein said amide comprises the reaction product of a carboxylic acid component and a polyamine component, wherein the charge mole ratio of the carboxylic acid component to the polyamine component is about 2:1 to 1:1, to form a molybdenum-containing reaction product. Preferably the molybdenum-containing reaction product is sulfurized to form the salt of a molybdenum oxysulfide or molybdenum sulfide and an amide.

Another aspect is directed to an oil soluble additive composition comprising the reaction product of:
(1) a molybdenum component which is, or is capable of forming, a molybdenum oxide, sulfide, or oxysulfide of the general formula $MoO_xS_y$ wherein $x \geq 0$, $y \geq 0$, and $12 \geq (x+y) \geq 2$; and
(2) an amide wherein said amide comprises the reaction product of a carboxylic acid component and a polyamine component, wherein the charge mole ratio of the carboxylic acid component to the polyamine component is about 2:1 to 1:1. In this aspect, a further embodiment when the molybdenum component which is, or capable of forming, a molybdenum sulfide, or oxysulfide can be further reacted after step (2) and under suitable reaction conditions with a component capable with reacting with active sulfur to thereby reduce the residual active sulfur of the oil soluble additive composition.

The following examples are presented to illustrate specific embodiments of this invention and are not to be construed in any way as limiting the scope of the invention

EXAMPLES

Example 1 (Comparative)

Salt of $MoO_xS_y$ and Isostearic Acid (ISA)/Tetraethylene Pentamine (TEPA) Polyamide
ISA/TEPA CMR=3.15:1
A round-bottom flask was charged with a polyamide of isostearic acid and tetraethylenepentamine (280 g, ISA/TEPA CMR=3.15), diluent oil (Exxon 100N, 90 g) and toluene (100 mL). Molybdenum trioxide (17.5 g, 0.12 mole) and water (25 g) were then added to the flask. The solution was heated at 70-90° C. for 3-4 hours. Sulfur (15 g, 0.46 mole) was then added to the solution and the mixture was heated at 100° C. for an additional 2 hours. The water and toluene were removed under vacuum. Analysis of the final product found the following: Mo=2.9 wt %; S=3.8 wt %.

Example 2

Salt of $MoO_xS_y$ Isostearic Acid (ISA)/Tetraethylenepentamine (TEPA) Polyamide
ISA/TEPA CMR=1.3:1
A round bottom flask was charged with a polyamide of isostearic acid and tetraethylenepentamine (10 g, ISA/TEPA CMR=1.3), diluent oil (Exxon 100N, 6.6 g) and toluene (40 mL). Molybdenum trioxide (1.3 g, 0.009 mole) and water (2 g) were then added to the flask. The solution was heated at 70-90° C. for 3-4 hours. Sulfur (0.55 g, 0.017 mole) was then added to the solution and the mixture was heated at 100° C. for an additional 2 hours. The water and toluene were removed under vacuum. Analysis of the final product found the following: Mo=4.0 wt %; S=3 wt %.

Example 3

Salt of $MoO_xS_y$ Isostearic Acid (ISA)/Diethylenetriamine (DETA) Polyamide
ISA/DETA CMR=1.7:1
A round-bottom flask was charged with a polyamide of isostearic acid and diethylenetriamine (250 g, ISA/DETA CMR=1.7), diluent oil (Exxon 100N, 363 g) and toluene (200 mL). Molybdenum trioxide (46.3 g, 0.32 mole) and water (25 g) were then added to the flask. The solution was heated at 70-90° C. for 3-4 hours. Ammonium sulfide (54.85 mL of a 42 wt % aqueous solution) was then added to the solution and the mixture was heated at 100° C. for an additional 2 hours. The water and toluene were removed under vacuum. Analysis of the final product found the following: Mo=3.56 wt %; S=2.03 wt %.

Example 4

Salt of $MoO_xS_y$ Isostearic Acid (ISA)/Diethylenetriamine (DETA) Polyamide
ISA/DETA CMR=1.3:1
A round-bottom flask was charged with a polyamide of isostearic acid and diethylenetriamine (400 g, ISA/DETA CMR=1.3), diluent oil (Exxon 100N, 385 g) and toluene (200 mL). Molybdenum trioxide (52.1 g, 0.36 mole) and water (40 g) were then added to the flask. The solution was heated at 70-90° C. for 3-4 hours. Sulfur (23.2 g, 0.72 mole) was then added to the solution and the mixture was heated at 100° C. for an additional 2 hours. The water and toluene were removed under vacuum. Analysis of the final product found the following: Mo=3.6 wt %.

Example 5

Salt of $MoO_xS_y$ Isostearic Acid (ISA)/Ethylenediamine (EDA) Polyamide
ISA/EDA CMR=1.0:1
A round-bottom flask was charged with a polyamide of ethylenediamine and isostearic acid (118 g, ISA/EDA CMR=1.0), diluent oil (Exxon 100N, 272 g) and toluene (360 mL). Molybdenum trioxide (18.9 g, 0.13 mole) and water (12 g) were then added to the flask. The solution was heated at 70-90° C. for 3-4 hours. Sulfur (8.4 g, 0.26 mole) was then added to the solution and the mixture was heated at 100° C. for an additional 2 hours. The water and toluene were removed under vacuum. Analysis of the final product found the following: Mo=3.0 wt %.

Lubricating Oil Compositions

Lubricating oil compositions containing salts of $MoO_xS_y$ and isostearic acid/polyamine amides were prepared from Examples 1 through 5 according to the following formulation:
(1) A salt of $MoO_xS_y$ and isostearic acid/polyamine amide (Mo content=500 ppm in each formulation)
(2) 4 wt % of an ashless dispersant
(3) 3.01 wt % of alkaline earth metal carboxylate detergent
(4) 0.60 wt % of alkaline earth metal sulfonate detergent
(5) 0.62 wt % of a zinc dialkyldithiophosphate
(6) 1.2 wt % of an antioxidant
(7) 4.3 wt % of a non-dispersant type viscosity index improver
(8) 5 ppm of a foam inhibitor
(9) The remainder was a lubricating oil Example 6 (Comparative)

Lubricating Oil Composition Containing Molybdenum Dithiocarbamate
A lubricating oil composition was prepared in accordance with the above formulations except that 0.82 wt % of a molybdenum dithiocarbamate (available as "Sakura Lube 505" from AdekaUSA Corporation, Saddle River, N.J.) served as the sole molybdenum source for this lubricating oil composition. The Mo content=500 ppm.

Example 7 (Comparative)

Lubricating Oil Composition Containing Molybdenum Oxysulfide/Monosuccinimide Complex
A lubricating oil composition was prepared in accordance with the above formulation except that 500 ppm of a molybdenum oxysulfide-monosuccinimide complex, derived from a polyisobutenyl (having a molecular weight of about 1000) monosuccinimide, as described in King et al, U.S. Pat. No. 4,263,152, served as the sole molybdenum source for this lubricating oil composition.
The compositions described above were tested for friction performance in a Mini-Traction Machine (MTM) bench test. The MTM is manufactured by PCS Instruments and operates in the pin-on-disk configuration in which a stainless steel ball (6 mm) is loaded against a rotating disk (32100 steel). The conditions employ a load of 10 Newtons, a speed of 500 mm/s, temperature of 120° C. and has a run-time of 60 minutes. The results are averaged for the last 10 minutes and are summarized in the Table 1.

TABLE 1

| Example | Description | CMR (ISA: Polyamine) | Coefficient of Friction (COF) (Last 10 Min Average) |
|---|---|---|---|
| 1 | $MoO_xS_y$/ISA/TEPA polyamide | 3.15 | 0.069 |
| 2 | $MoO_xS_y$/ISA/TEPA polyamide | 1.3 | 0.045 |
| 3 | $MoO_xS_y$/ISA/DETA polyamide | 1.7 | 0.049 |

TABLE 1-continued

| Example | Description | CMR (ISA: Polyamine) | Coefficient of Friction (COF) (Last 10 Min Average) |
|---|---|---|---|
| 4 | MoO$_x$S$_y$/ISA/DETA polyamide | 1.3 | 0.044 |
| 5 | MoO$_x$S$_y$/ISA/EDA amide | 1.0 | 0.042 |
| 6 | MoDTC | — | 0.044 |
| 7 | MoO$_x$S$_y$-succinimide | — | 0.104 |

Examples 2-5 in Table 1 show that the coefficient of friction (wherein the lower the COF, the better the friction reducing properties) of the lubricating oil composition of the present invention is comparable to that of molybdenum dithiocarbamate, a well known friction reducer, when the salt of the molybdenum component and the carboxylic acid/polyamine component had a carboxylic acid: polyamine CMR of from about 2:1 to about 1:1. Examples 2-5 also exhibit superior friction reducing properties as compared to a molybdenum succinimide complex (e.g., Example 7). Moreover, Examples 2-5 show better friction reducing properties than Example 1 (comparative), which comprises a lubricating oil additive which had an ISA:TEPA CMR of 3.15:1. As evidenced by the data in Table 1, friction reducing properties are improved when the CMR of isostearic acid to polyalkylene polyamine is lowered.

Example 8

To a 2 L glass reactor, a polyamide of isostearic acid and diethylenetriamine (467.3 g, ISA/DETA CMR=1.7, TBN=117 mg KOH/g measured by ASTM D2896) and Chevron 100N base oil (911.0 g) were charged. The reactor was heated at 70° C. under nitrogen blanket and agitation. Molybdenum trioxide (103.2 g, 0.72 mole) and water (88.8 g) were charged to above solution. Reaction temperature was ramped to 90-95° C. and held for 3 hours to allow the completion of molybdation reaction. Elemental sulfur (34.4 g, 1.07 mole) was then charged to the reactor under vigorous agitation. Reaction temperature was ramped to 120° C., and N$_2$ was changed to sweep at the flowrate of 180-200 mL/min. The mixture was held at 120° C. for 2 hours to complete the sulfurization reaction. Analysis of the product found the following: Mo=4.0 wt %, S=2.0 wt %.

Example 9

472.0 g of the sulfurized oil soluble molybdenum complex prepared in Example 8, were added to a reactor. A polyamide of isostearic acid and diethylenetriamine (14.4 g, ISA/DETA CMR=1.7) was then further charged to the reactor to start step c). Under vigorous agitation, the above mixture was heated at 120° C. for 2 hours under nitrogen sweep (180-200 mL/min) The resulting composition was measured for copper strip corrosion in ASTM D130 test with results in Table 2.

Example 10

419.9 g of the sulfurized oil soluble molybdenum complex prepared in Example 8, were added to a reactor. A polyamide of isostearic acid and diethylenetriamine (25.2 g, ISA/DETA CMR=1.7) was then further charged to the reactor to start step c). Under vigorous agitation, the above mixture was heated at 120° C. for 2 hours under nitrogen sweep (180-200 mL/min) Then the nitrogen sweep was stopped, air was introduced at the flowrate of 180-200 mL/min to sparge the mixture at 120° C. for an additional one hour. The resulting composition was measured for copper strip corrosion in ASTM D130 test with results in Table 2.

Example 11

410.2 g of the sulfurized oil soluble molybdenum complex prepared in Example 8, were added to a reactor. A polyamide of isostearic acid and diethylenetriamine (41.0 g, ISA/DETA CMR=1.7) was then further charged to the reactor. Under vigorous agitation, the above mixture was heated at 120° C. for 2 hours under nitrogen sweep (180-200 mL/min). The resulting composition was measured for copper strip corrosion in ASTM D130 test with results in Table 2.

Example 12

A polyamide of isostearic acid and diethylenetriamine (450.0 g, ISA/DETA CMR=1.7) and Chevron 100N base oil (877.2 g) were charged to a 2 L glass reactor. The reactor was heated at 70° C. under nitrogen blanket and agitation. Molybdenum trioxide (99.4 g, 0.69 mole) and water (85.5 g) were then added to above solution. Reaction temperature was ramped to 85-90° C. and held for 3 hours to allow the completion of molybdation reaction. Elemental sulfur (32.7 g, 1.02 mole) was charged to the reactor under vigorous agitation. Reaction temperature was ramped to 120° C., and N$_2$ was changed to sweep at the flowrate of 180-200 mL/min. The mixture was held at 120° C. for 2 hours to complete the sulfurization reaction. Oleylamine (147.2 g) was then charged to the reactor and it was kept at 120° C. At the same time, air was sparged through the reactor at the flowrate of 180-200 mL/min under vigorous agitation for 5 hours. Analysis found the following: Mo=4.0 wt %, S=2.0 wt %. Color<3.5 (Measured by ASTM D6045 directly on the oil containing other lubricating additives and the prepared molybdenum-containing additive in an amount of 500 ppm by mass of molybdenum: the lower the reading the lighter the sample).

The Copper Strip Corrosion (ASTM D130) results at 100° C. and 121° C. for above examples are shown in Table 2.

TABLE 2

Comparison of Copper Strip Corrosion with and without step c)

| Example | Description of compound capable of reacting with active sulfur | Amount (wt %) | Cu Strip Corrosion At 100° C. 3 hours | At 121° C 3 hours |
|---|---|---|---|---|
| 8 | None | | 3B | 2C |
| 9 | ISA/DETA polyamide (1.7 CMR) | 3 | 1B | 3A |
| 10 | ISA/DETA polyamide (1.7 CMR) | 6 | 1A | 1B |
| 11 | ISA/DETA polyamide (1.7 CMR) | 10 | 1A | 1B |
| 12 | Oleylamine | 10 | 1A | 1A |

Illustrated in Table 2, Examples 9-12 which further include the reaction of a fatty acid polyamide (ISA/DETA polyamine) or a fatty acid amine (oleylamine) to reduce the active sulfur in the sulfurized oil soluble molybdenum complex have a dramatic effect on the copper strip corrosion test.

Example 13

A polyamide of isostearic acid and diethylenetriamine (483.9 g, ISA/DETA CMR=1.7) and Chevron 100N base oil (931.3 g) were charged to a 2 L glass reactor. The reactor was then heated at 70° C. under nitrogen blanket and agitation. Molybdenum trioxide (106.9 g, 0.74 mole) and water (91.9 g) were charged to above solution. Reaction temperature was ramped to 90-95° C. and held for 3 hours to complete the molybdation reaction. Elemental sulfur (47.5 g, 1.48 mole) was then charged to the reactor under vigorous agitation. Reaction temperature was ramped to 120° C., and $N_2$ was changed to sweep at the flowrate of 280-300 mL/min. The mixture was held at 120° C. for 2-3 hours to allow the completion of sulfurization reaction. Color was measured by ASTM D6045 at a value of <5.5 measured directly on the oil containing other lubricating additives and the above prepared molybdenum containing additive in an amount of 500 ppm by mass of molybdenum: the lower the reading the lighter the sample. The final product is calculated to have the following: Mo=4.3 wt %, S=2.9 wt %.

Example 14

A polyamide of isostearic acid and diethylenetriamine (131.3 g, ISA/DETA CMR=1.7) and Chevron 100N base oil (252.6 g) were charged to a 500 ml glass reactor. The reactor was then heated at 70° C. under nitrogen blanket and agitation. Molybdenum trioxide (29.0 g, 0.20 mole) and water (24.93 g) were charged to above solution. Reaction temperature was ramped to 90° C. and held for 3 hours to complete the molybdation reaction. Elemental sulfur (12.9 g, 0.40 mole) was then charged to the reactor under vigorous agitation. Reaction temperature was ramped to 120° C., and $N_2$ was changed to sweep at the flowrate of 150-160 mL/min. The mixture was held at 120° C. for 3 hours to allow the completion of sulfurization reaction. Color was measured by ASTM D6045 at a value of 4, measured directly on the oil containing other lubricating additives and the above prepared molybdenum containing additive in an amount of 500 ppm by mass of molybdenum: the lower the reading the lighter the sample. Analysis of the final product found the following: Mo=4.6 wt %, S=2.9 wt %.

Example 15

To a 500 ml glass reactor, a polyamide of isostearic acid and diethylenetriamine (124.3 g, ISA/DETA CMR=1.7) and Chevron 100N base oil (242.3 g) were charged. The reactor was heated at 70° C. under nitrogen blanket and agitation. Molybdenum trioxide (27.5 g, 0.19 mole) and water (17.7 g) were charged to above solution. Reaction temperature was ramped to 85-90° C. and held for 3 hours to complete the molybdation reaction. Elemental sulfur (9.0 g, 0.28 mole) was then charged to the reactor under vigorous agitation. Reaction temperature was ramped to 120° C., and $N_2$ was switched to sweep at the flowrate of 140-160 mL/min. The mixture was held at 120° C. for 2 hours to allow the completion of sulfurization reaction. Oleylamine (40.7 g) was then charged to the reactor at 120° C. At the same time, air was sparged through the reactor at the flowrate of 90-100 mL/min under vigorous agitation for 4 hours. Color was measured by ASTM D6045 at a value of 3.5, measured directly on the oil containing other lubricating additives and the above prepared molybdenum containing additive in an amount of 500 ppm by mass of molybdenum: the lower the reading the lighter the sample. The Mo and S content of the product was calculated to have following: Mo=4.1 wt %, S=2.1 wt %.

Example 16

A polyamide of isostearic acid and diethylenetriamine (138.2 g, ISA/DETA CMR=1.7) and Chevron 100N base oil (224.1 g) were added to a 500 ml glass reactor, The reactor was heated at 70° C. under nitrogen blanket and agitation. Molybdenum trioxide (30.5 g, 0.21 mole) and water (26.2 g) were charged to above solution. Reaction temperature was ramped to 90° C. and held for 3 hours to complete the molybdation reaction. Elemental sulfur (10.2 g, 0.32 mole) was charged to the reactor under vigorous agitation. Reaction temperature was ramped to 120° C., and $N_2$ was switched to sweep at the flowrate of 80-100 mL/min. The mixture was held at 120° C. for 2 hours to allow the completion of sulfurization reaction. Oleylamine (20.3 g) and Chevron 100N base oil (20.3 g) were then charged to the reactor at 120° C. At the same time, air was sparged through the reactor at the flowrate of 80-100 mL/min under vigorous agitation for 4 hours. Color was measured by ASTM D6045 at a value of 4, measured directly on the oil containing other lubricating additives and the above prepared molybdenum containing additive in an amount of 500 ppm by mass of molybdenum: the lower the reading the lighter the sample. The Mo and S content of the product was calculated to have following: Mo=4.5 wt %, S=2.3 wt %.

Table 3 shows the effect of color and viscosity by step c) on prepared molybdenum-containing additive.

TABLE 3

Effect of step c) on the viscosity and color of prepared molybdenum containing additive

| Example | Color measured by ASTM D6045[a] | Viscosity[b] cSt at 60° C. | Viscosity[b] cSt at 70° C. |
|---------|---------------------------------|----------------------------|----------------------------|
| 14      | 4.0                             | 1247                       | 339                        |
| 15      | 3.5                             | 229                        | 120                        |
| 16      | 3.5                             | 520                        | 223                        |

[a]Color was measured by ASTM D6045 directly on the oil containing other lubricating additives and the prepared molybdenum containing additive in an amount of 500 ppm by mass of molybdenum: the lower the reading the lighter the sample.
[b]Viscosity was measured by ASTM D445 for the prepared molybdenum containing additive.

As illustrated by Examples 15 and 16, the subsequent addition of oleylamine to the sulfurized oil soluble molybdenum complex improves the color from a 4.0 to a 3.5 in the ASTM D6045 measurement and quite unexpectedly demonstrates a viscosity benefit as measured in the ASTM D445 test.

What is claimed is:
1. A process for preparing a sulfurized oil soluble molybdenum complex having reduced active sulfur comprising:
   a. reacting an acidic molybdenum compound with a first basic nitrogen derived from an amide reaction product of a $C_{4-40}$ aliphatic carboxylic acid component and a polyamine having 2 to 10 nitrogen atoms; wherein the charge mole ratio of the carboxylic acid component to the polyamine component is about 2:1 to 1:1;
   b. reacting the product of step a) with a sulfur-containing compound in amounts to provide a sulfurized oil soluble molybdenum complex having 1 to 4 moles of sulfur per mole of molybdenum and active sulfur; and
   c. reacting the product of step b) with at least one compound capable of reacting with the active sulfur of step b) to thereby reduce the active sulfur in the product of step b), wherein the compound capable of reacting with the active sulfur of step b) is a second basic nitrogen-containing compound.
2. The process of claim 1, wherein the charge mole ratio of the carboxylic acid component to the polyamine component is about 1.7:1 to 1:1.

3. The process of claim 1, wherein the charge mole ratio of the carboxylic acid component to the polyamine component is about 1.7:1 to 1.3:1.

4. The process of claim 1, wherein the polyamine is a polyalkylenepolyamine of the general formula

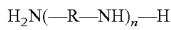

and wherein R is an alkylene group of 2-3 carbon atoms and n is an integer of from 1 to 11.

5. The process of claim 4, wherein the polyamine is tetraethylenepentamine (TEPA), diethylenetriamine (DETA), ethylenediamine (EDA), or mixtures thereof.

6. The process of claim 1, wherein in step a) from 0.2 to 1 atoms of molybdenum are present per basic nitrogen atom.

7. The process of claim 6, wherein in step a) from 0.2 to 0.7 atoms of molybdenum are present per basic nitrogen atom.

8. The process of claim 1, wherein the carboxylic acid component is a saturated monocarboxylic fatty acid.

9. The process of claim 8 wherein the carboxylic acid component is selected from the group consisting of isostearic acid, stearic acid, lauric acid, myrstic acid, palmitic acid, and arachidic acid.

10. The process of claim 1, wherein said reaction of step a) is conducted in the presence of a polar promoter.

11. The process of claim 10, wherein the polar promoter is selected from the group consisting of 1,3-propanediol, 1,4-butanediol, diethylene glycol, butyl cellosolve, propylene glycol, 1,4-butyleneglycol, methyl carbitol, ethanolamine, ammonium hydroxide, alkyl ammonium hydroxide, metal hydroxide, N-methyl-diethanol-amine, dimethyl formamide, N-methyl acetamide, dimethyl acetamide, methanol, ethylene glycol, dimethyl sulfoxide, hexamethyl phosphoramide, tetrahydrofuran, water, inorganic acid, and mixtures thereof.

12. The process of claim 11, wherein the polar promoter is water.

13. The process of claim 1, wherein step b) is carried out with the sulfur-containing compound selected from sulfur, hydrogen sulfide, phosphorus pentasulfide, $R_2S_x$ where R is $C_{1-10}$alkyl, and x is at least 2, inorganic sulfides or inorganic polysulfides, thioacetamide, thiourea, mercaptans of the formula RSH where R is $C_{1-10}$alkyl, or a sulfur-containing antioxidant.

14. The process of claim 1, wherein the molybdenum component is selected from the group consisting of molybdic acid, ammonium molybdate, sodium molybdate, potassium molybdate, $MoOCl_4$, $MoO_2Br_2$, $Mo_2O_3Cl_6$, molybdenum trioxide, and mixtures thereof.

15. The process of claim 14, wherein the molybdenum component is molybdenum trioxide.

16. The process of claim 1 wherein the second basic nitrogen-containing compound is selected from at least one amine or amide.

17. The process of claim 16 wherein the second basic nitrogen-containing compound is an amide which is the reaction product of at least one fatty acid with at least one polyalkylene polyamine.

18. A process for preparing a sulfurized oil soluble molybdenum complex having reduced active sulfur comprising:
   a. reacting an acidic molybdenum compound with a first basic nitrogen derived from an amide reaction product of a $C_{4-40}$ aliphatic carboxylic acid component and a polyamine having 2 to 10 nitrogen atoms; wherein the charge mole ratio of the carboxylic acid component to the polyamine component is about 2:1 to 1:1;
   b. reacting the product of step a) with a sulfur-containing compound in amounts to provide a sulfurized oil soluble molybdenum complex having 1 to 4 moles of sulfur per mole of molybdenum and active sulfur; and
   c. reacting the product of step b) with at least one compound capable of reacting with the active sulfur of step b) to thereby reduce the active sulfur in the product of step b), wherein the compound capable of reacting with the active sulfur in step c) is an alkali metal sulfide.

19. A lubricating oil composition comprising an oil of lubricating viscosity and the product produced by the process of claim 1.

20. A lubricating oil composition comprising an oil of lubricating viscosity and the product produced by the process of claim 18.

21. The process of claim 1 wherein the second basic nitrogen-containing compound is oleylamine.

22. The process of Claim 1 wherein the first basic nitrogen derived from the amide reaction product and the second basic nitrogen-containing compound are the same.

* * * * *